(12) United States Patent
Tang et al.

(10) Patent No.: US 11,253,592 B2
(45) Date of Patent: Feb. 22, 2022

(54) WATER-SOLUBLE COMPOUNDS WITH AGGREGATION-INDUCED EMISSION CHARACTERISTICS

(71) Applicant: THE HONG KONG UNIVERSITY OF SCIENCE AND TECHNOLOGY, Hong Kong (CN)

(72) Inventors: Benzhong Tang, Hong Kong (CN); Dong Wang, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 34 days.

(21) Appl. No.: 16/758,697

(22) PCT Filed: Oct. 24, 2018

(86) PCT No.: PCT/CN2018/111636
§ 371 (c)(1),
(2) Date: Apr. 23, 2020

(87) PCT Pub. No.: WO2019/080868
PCT Pub. Date: May 2, 2019

(65) Prior Publication Data
US 2020/0338196 A1    Oct. 29, 2020

Related U.S. Application Data

(60) Provisional application No. 62/707,135, filed on Oct. 24, 2017.

(51) Int. Cl.
| | | |
|---|---|---|
| *A61K 41/00* | (2020.01) | |
| *A61B 90/20* | (2016.01) | |
| *A61N 5/06* | (2006.01) | |
| *C07D 409/06* | (2006.01) | |
| *C09K 11/07* | (2006.01) | |
| *G01N 21/64* | (2006.01) | |
| *G01N 21/76* | (2006.01) | |
| *G02B 21/00* | (2006.01) | |
| *G02B 21/16* | (2006.01) | |
| *C07D 215/12* | (2006.01) | |

(52) U.S. Cl.
CPC .......... *A61K 41/0057* (2013.01); *A61B 90/20* (2016.02); *A61N 5/062* (2013.01); *C07D 215/12* (2013.01); *C07D 409/06* (2013.01); *C09K 11/07* (2013.01); *G01N 21/6458* (2013.01); *G01N 21/76* (2013.01); *G02B 21/0076* (2013.01); *G02B 21/16* (2013.01); *A61N 2005/0662* (2013.01); *C09K 2211/1018* (2013.01)

(58) Field of Classification Search
None
See application file for complete search history.

(56) References Cited

FOREIGN PATENT DOCUMENTS

| | | |
|---|---|---|
| CN | 106631997 A | 5/2017 |
| CN | 107001927 A | 8/2017 |

*Primary Examiner* — Joseph R Kosack
(74) *Attorney, Agent, or Firm* — Nath, Goldberg & Meyer; Joshua B. Goldberg

(57) ABSTRACT

The present subject matter relates to water-soluble, fluorescent compounds that have aggregation-induced emission (AIE) characteristics and exhibit near infrared (NIR) absorption. The compounds can be utilized as plasma-membrane specific bio-probes in cell imaging through a wash-free and fast staining procedure. In addition, the compounds can efficiently generate reactive oxygen species (ROS) in vivo when irradiated with visible light. As such, the compounds can be effective in killing cancer cells through image-guided, photodynamic therapy (PDT) processes.

20 Claims, 8 Drawing Sheets

| Solvent | $\lambda_{em}$ (nm) |
|---|---|
| Chloroform | 679 |
| Dioxane | 634 |
| DCM | 674 |
| THF | 676 |
| EtOH | 695 |
| DMSO | 696 |
| MeOH | 699 |
| Acetone | n.d. |
| ACN | n.d. |
| H$_2$O | n.d. |
Fig. 7B
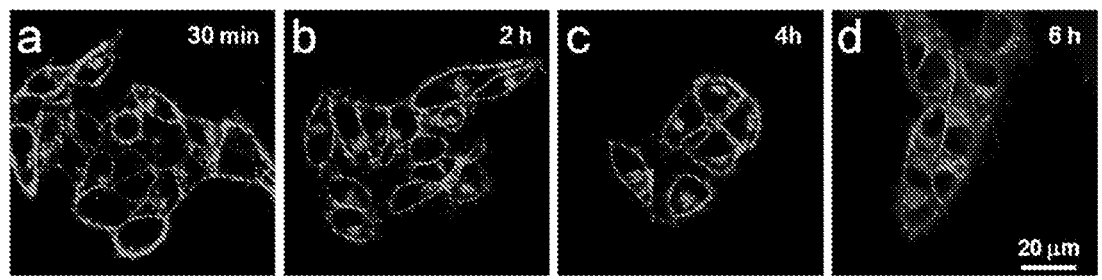
Fig. 8A-8D
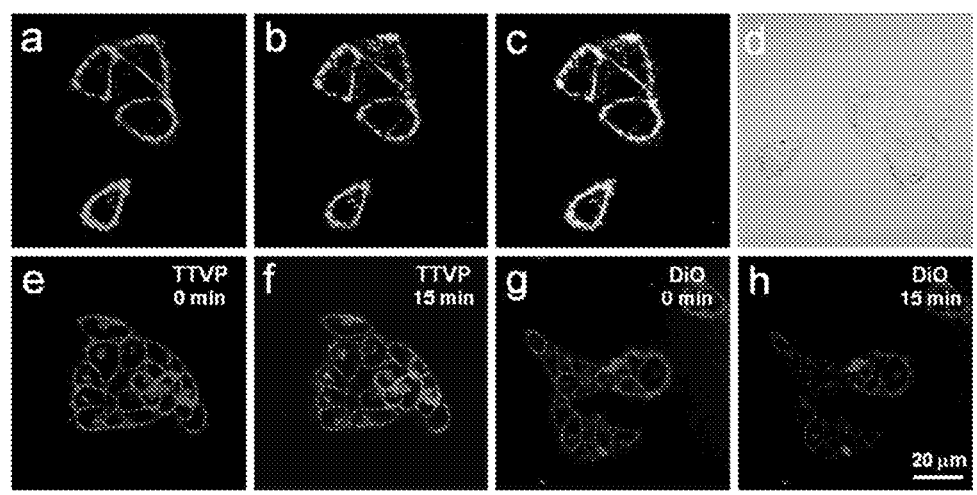
Fig. 9A-9H

WATER-SOLUBLE COMPOUNDS WITH AGGREGATION-INDUCED EMISSION CHARACTERISTICS

CROSS-REFERENCE

The present application claims priority to provisional U.S. Patent Application No. 62/707,135, filed Oct. 24, 2017, which was filed by the inventors hereof and is incorporated herein by reference in its entirety.

FIELD

The present subject matter relates generally to a series of fluorescent compounds with aggregation-induced emission characteristics and near infrared absorption and their applications in bioimaging and phototheranostics.

BACKGROUND

Fluorescent bioimaging is a powerful and non-invasive analytical tool for visualizing a biological species, providing fast response, excellent temporal resolution, superb sensitivity, in-situ workability, ease of operation, and good reproducibility. As a major branch of fluorescent materials, small organic fluorophores, particularly fluorophores with near infrared (NIR) emission (>700 nm), possess distinct advantages, such as high penetration depth, low biological autofluorescence interference, minimal photodamage to biological structures, and reduced light scattering. However, owing to the J-J stacking and other non-radiative pathways, conventional NIR fluorophores are typically either weakly emissive or non-emissive in high concentration or in the aggregation state.

Organic molecules naturally aggregate in biological media owing to the high hydrophobicity of their emitting centers. This phenomenon, known as aggregation-caused quenching (ACQ), is quite common and remains the major barrier to implementing practical applications of many conventional NIR fluorophores in the fields of bioimaging and theranostics.

Interestingly, the emergence of a novel class of NIR fluorophores with aggregation-induced emission (AIE) characteristics solves the ACQ problem. AIE luminogens (AIEgens) are non-emissive when molecularly dissolved in solvents, but are induced to fluoresce intensely in aggregate. This AIE feature permits use of the fluorophores with any concentration, and enables development of fluorescent "light-up" probes for biosensing and imaging applications.

Until now, only a handful of AIEgens exhibiting high-performance NIR emission have been developed and used in biological study. Although some water-soluble AIEgens with short-wavelength emissions have been prepared and employed as powerful bioprobes, those luminogens were not NIR AIEgens.

In vitro cellular imaging is one of the most widely used applications of fluorescent bio-imaging. As an important cell organelle, the plasma membrane has a phospholipid bilayer that is a protective two-dimensional boundary between a living cell and its surroundings. The plasma membrane has been involved in various cellular processes and bio-functions, such as cell signaling, cell adhesion, endocytosis, exocytosis and selective permeation of substances. The abnormality of plasma membrane in cells is a critical biomarker for cell status and many diseases. Therefore, visualizing plasma membranes by fluorescent bio-probes is important and useful. However, previously developed plasma membrane-specific fluorophores (such as DiO, DiI, and CellMask) have their respective and collective drawbacks, including short emission wavelengths, small Stokes shifts, requirement of hazardous organic solvents for preparing stock solution, long incubation period and tedious washing procedures after cell staining. In particular, the latter two have long been key issues in cellular fluorescence imaging. Long incubation is time-consuming, and often causes nonspecific illumination of cellular components. Aiming to improve the signal-to-noise (S/N) ratio of cell imaging, a washing process after cell staining is usually required for eliminating the strong residual signal from the free dyes. The post-washing process could result in some problems, for instance, delaying the acquisition of microscopic data and decreasing the accuracy of cell-imaging results due to both the altered cellular environment and the loss of cells. Moreover, the washing procedure is incompatible with continuous sensing or monitoring of biological processes. A novel fluorescent plasma membrane probe that overcomes the above-mentioned deficiencies is urgently needed.

Dual applications in simultaneous imaging and therapy have attracted significant scientific interest. As an appropriate and gentle approach for cancer therapy, photodynamic therapy (PDT) has been clinically approved for eliminating malignant tumor cells with minimal invasion and precise controllability. Plasma membrane is considered to be a wonderful cellular targeting site for implementing PDT, because plasma membrane is strongly related with various bio-functions and cellular processes. In addition, plasma membrane is the outermost protection layer of cells, in which its destruction is fatal to cells, and light energy can be maximally utilized. However, almost all of the previously reported plasma membrane-staining fluorophores can only be used as imaging probes instead of having dual applications in simultaneous imaging and therapy. A photosensitizer with high generation efficiency of reactive oxygen species (ROS) is essentially necessary for PDT application. AIEgens that can promote both fluorescence and ROS generation can provide dual applications in simultaneous imaging and PDT.

Accordingly, NR AIEgens with good water-solubility which can be used both as plasma membrane-specific bio-probes and in cancer phototheranostics are highly desirable.

SUMMARY

The present subject matter relates to water-soluble, fluorescent compounds that have aggregation-induced emission (AIE) characteristics and exhibit near infrared (NR) absorption. The compounds can be utilized as plasma-membrane specific bio-probes in cell imaging through a wash-free and fast staining procedure. In addition, the compounds can efficiently generate reactive oxygen species (ROS) in vivo when irradiated with visible light. As such, the compounds can be effective in killing cancer cells through image-guided, photodynamic therapy (PDT) processes.
In an embodiment, the compounds have a backbone structural formula selected from the group consisting of:
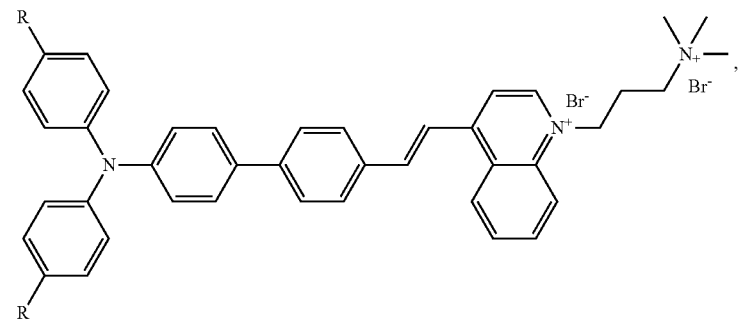
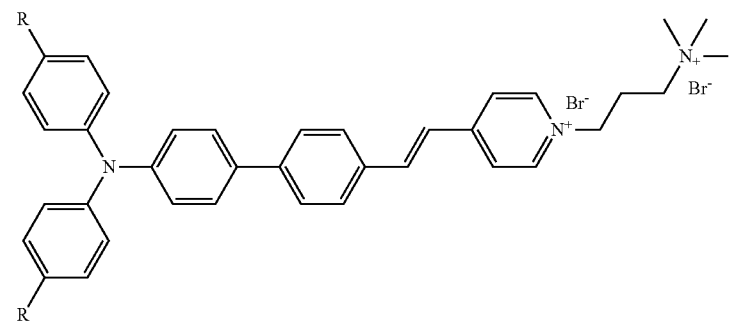
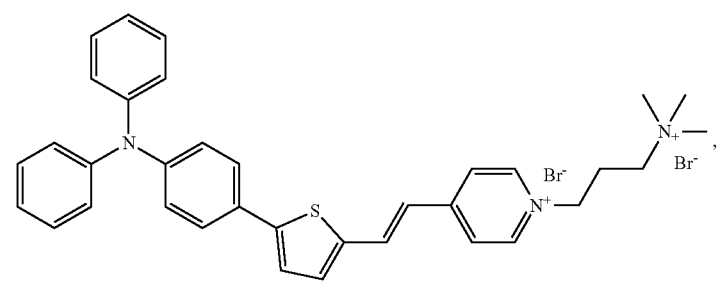
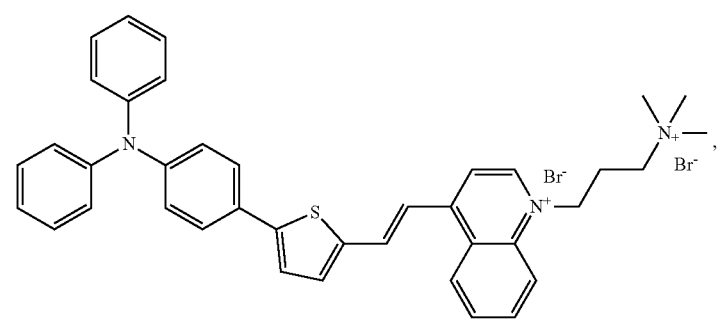

-continued
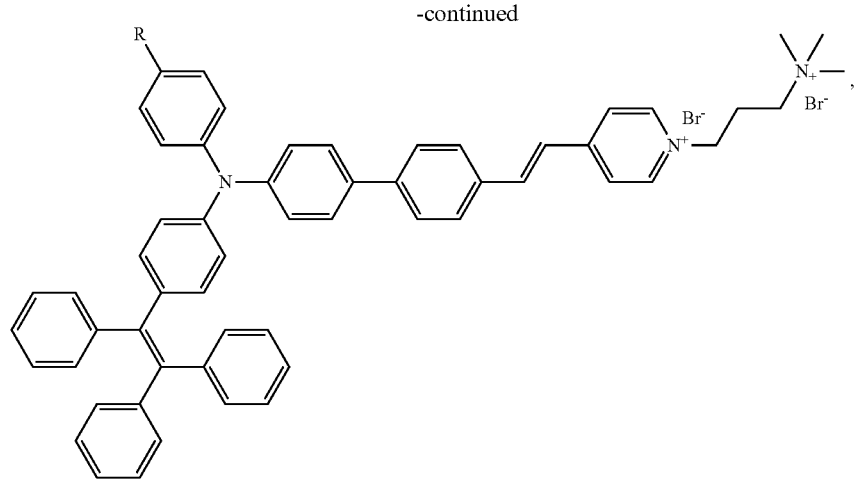
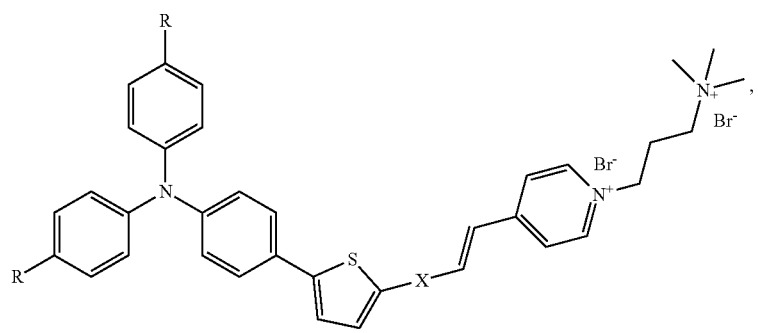
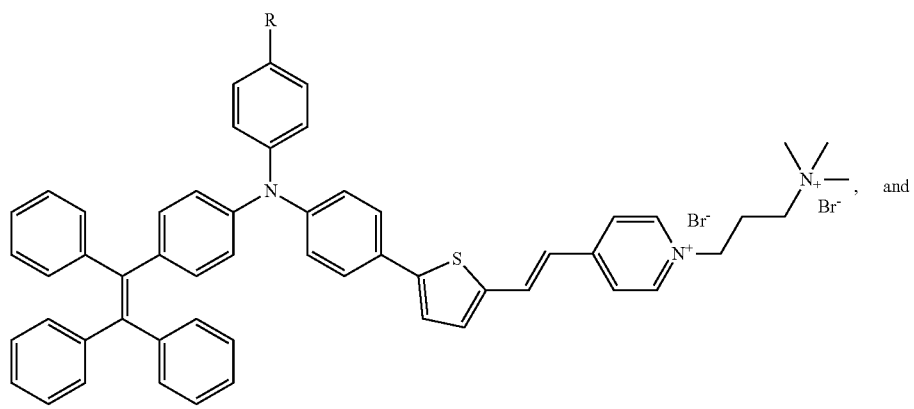
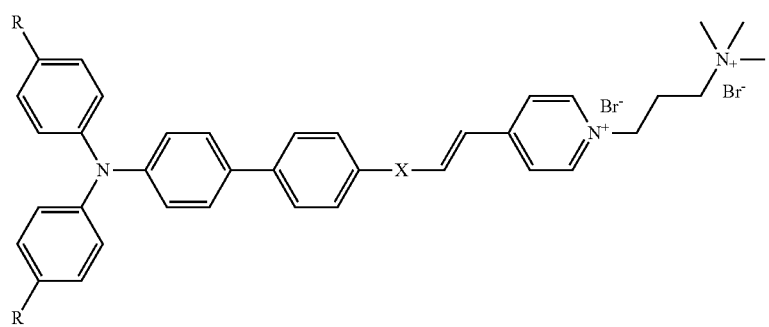

wherein each R is independently selected from the group consisting of H, alkyl, unsaturated alkyl, heteroalkyl, cycloalkyl, heterocycloalkyl, aryl, heteroaryl, alkyl-NCS, alkyl-$N_3$ and alkyl-$NH_2$; and wherein X is selected from the group consisting of phenyl, heteroaryl, and C=C.

In a further embodiment, the compound is:

BRIEF DESCRIPTION OF DRAWINGS

Various embodiments will now be described in detail with reference to the accompanying drawings.

FIG. 7B depicts data of emission maximum in FIG. 7A.

FIGS. 8A-8D depict confocal images of HeLa cells stained with TTVP for different times (Concentration: 500 nM. Scale bar=20 μm. $\lambda_{ex}$: 488 nm (1% laser power, 0.05 μW)).

FIG. 9A depicts confocal images of HeLa cells stained with TTVP.

FIG. 9B depicts confocal images of HeLa cells stained with DiO.

FIG. 9C depicts merged images of panels in FIG. 9A and FIG. 9B.

FIG. 9D depicts bright-field images of the HeLa cells.

FIG. 9E depicts confocal images of HeLa cells stained with TTVP before laser irradiation.

FIG. 9F depicts confocal images of HeLa cells stained with TTVP after laser irradiation for 15 minutes (λex: 488 nm (1% laser power, 0.05 μW; Scale bar=20 μm)).

FIG. 9G depicts confocal images of HeLa cells stained with DiO.

FIG. 9H depicts confocal images of HeLa cells stained with DiO after laser irradiation for 15 minutes (λex: 488 nm (1% laser power, 0.05 μW). Scale bar=20 μm).

DETAILED DESCRIPTION

Figures 1A, 1B:
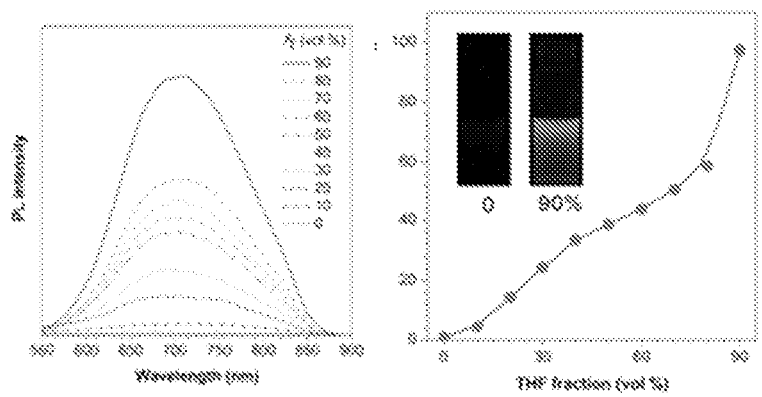
FIG. 1A depicts PL spectra of TTVP in water/THF mixtures with different THF fractions ($f_T$) (Concentration: 10 μM; excitation wavelength: 515 nm).
FIG. 1B depicts plot of PL intensity versus the composition of the water/THF mixtures of TTVP (Inset: Fluorescence photographs of TTVP in the aqueous solution and in water/THF mixtures with 90% THF fractions under 365 nm UV irradiation).

The following definitions are provided for the purpose of understanding the present subject matter and for constructing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise.

It should be understood that the order of steps or order for performing certain actions is immaterial so long as the present teachings remain operable. Moreover, two or more steps or actions may be conducted simultaneously.

The term "$\lambda_{ex}$" as used herein refers to excitation wavelength.

The phrase "aggregation caused quenching" or "ACQ" as used herein refers to the phenomenon wherein the aggregation of π-conjugated fluorophores significantly decreases the fluorescence intensity of the fluorophores. The aggregate formation is said to "quench" light emission of the fluorophores.

The phrase "aggregation induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

"Emission intensity" as used herein refers to the magnitude of fluorescence/phosphorescence normally obtained from a fluorescence spectrometer or fluorescence microscopy measurement; "fluorophore" or "fluorogen" as used herein refers to a molecule which exhibits fluorescence; "luminogen" or "luminophore" as used herein refers to a molecule which exhibits luminescence; and "AIEgen" as used herein refers to a molecule exhibiting AIE characteristics.

As used herein, "halo" or "halogen" refers to fluoro, chloro, bromo, and iodo.

As used herein, "alkyl" refers to a straight-chain or branched saturated hydrocarbon group. Examples of alkyl groups include methyl(Me), ethyl(Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine Noxide thiophene S-oxide, thiophene S,S-dioxide). Examples of heteroaryl groups include, for example, the 5- or 6-membered monocyclic and 5-6 bicyclic ring systems shown below:

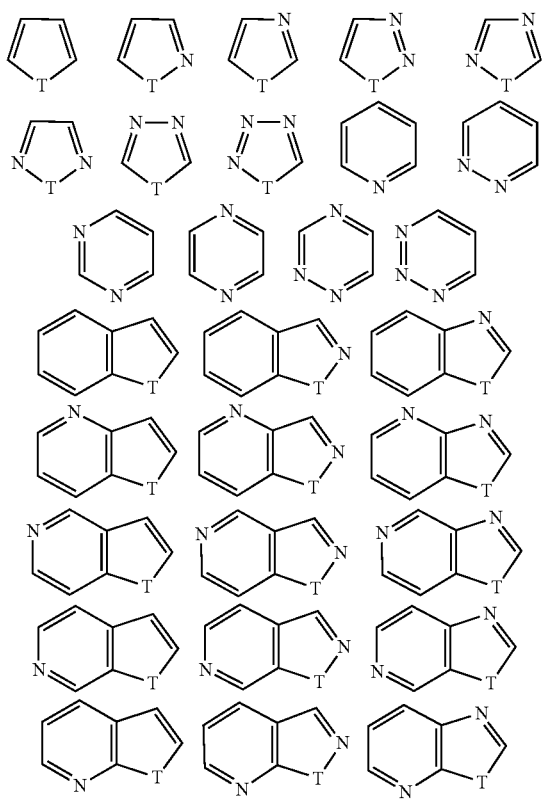

where T is O, S, NH, N-alkyl, N-aryl, N-(arylalkyl) (e.g., N-benzyl), SiH2, SiH(alkyl), Si(alkyl)2, SiH(arylalkyl), Si(arylalkyl)2, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

As used herein, a "donor" material refers to an organic material, for example, an organic nanoparticle material, having holes as the majority current or charge carriers.

As used herein, an "acceptor" material refers to an organic material, for example, an organic nanoparticle material, having electrons as the majority current or charge carriers.

As used herein, a "theranostic agent" refers to an organic material, for example, an organic nanoparticle material, having both diagnostic and therapeutic capabilities.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Fluorescent Compounds

The present subject matter relates to water-soluble, fluorescent compounds that have aggregation-induced emission (AIE) characteristics and exhibit near infrared (NIR) absorption. The present compounds can be beneficial in both diagnostic and phototheranostic applications, particularly with respect to detecting abnormalities in the plasma membrane of cells and photodynamic cancer therapy.
In an embodiment, the compounds have a backbone structural formula selected from the group consisting of:
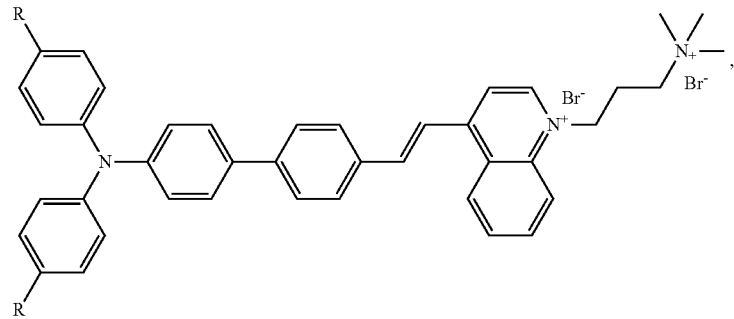
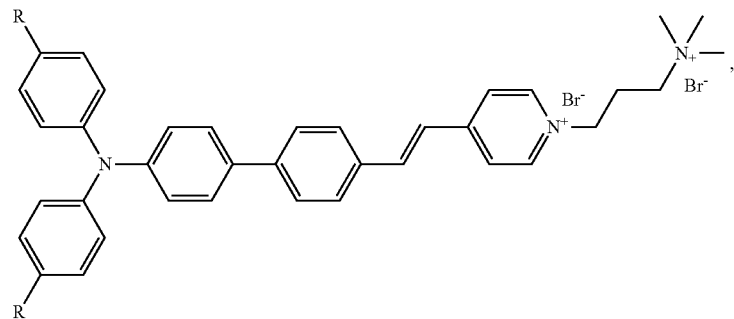
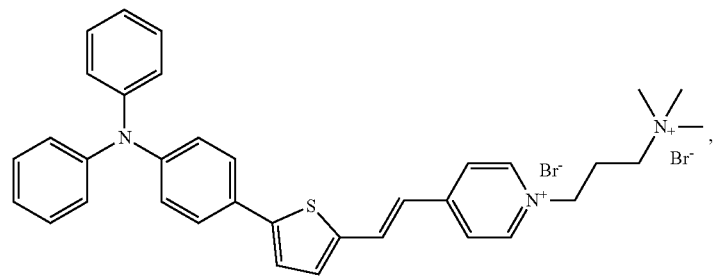
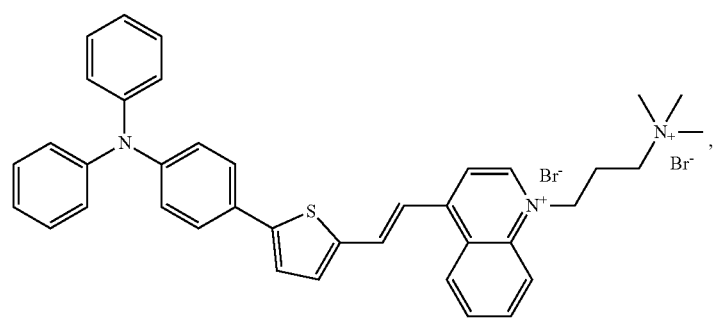

-continued
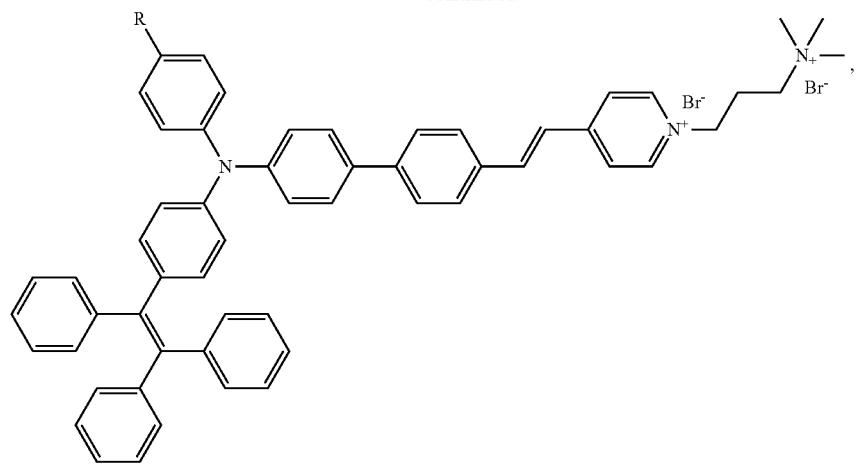
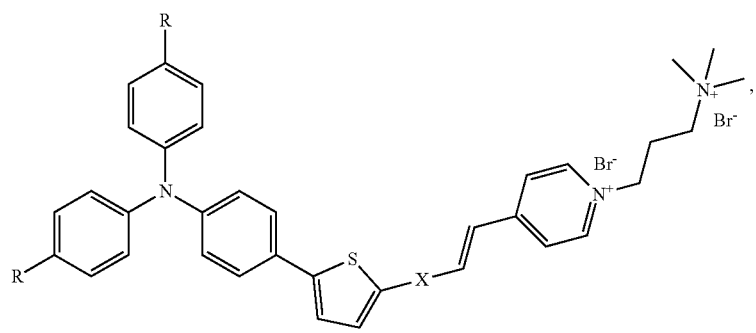
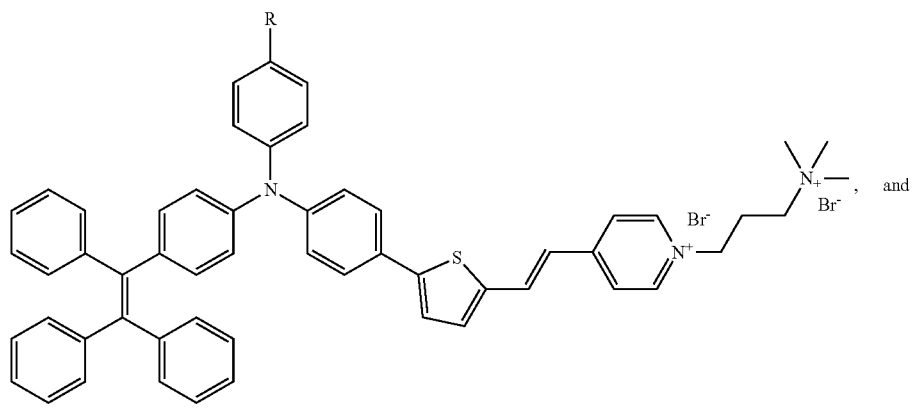
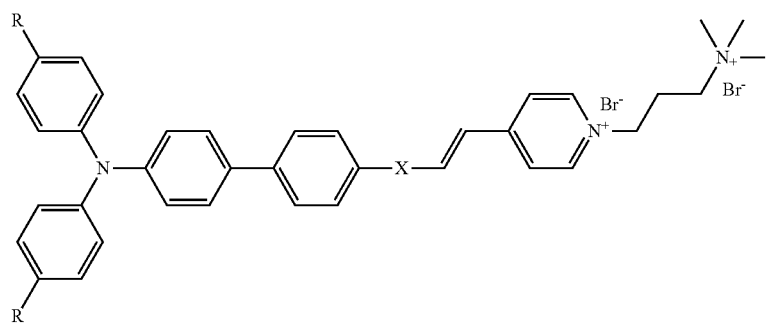

wherein each R is independently selected from the group consisting of H, alkyl, unsaturated alkyl, heteroalkyl, cycloalkyl, heterocycloalkyl, aryl, heteroaryl, alkyl-NCS, alkyl-N$_3$ and alkyl-NH$_2$; and wherein X is selected from the group consisting of phenyl, heteroaryl, and C=C.

In a further embodiment, the compound is:

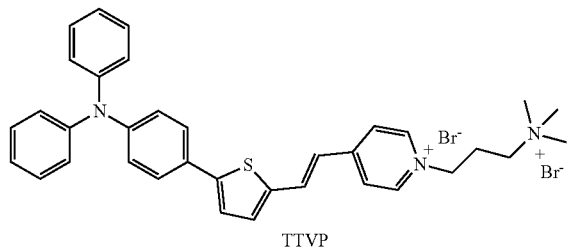

TTVP

An exemplary reaction scheme for preparing TTVP is provided below:

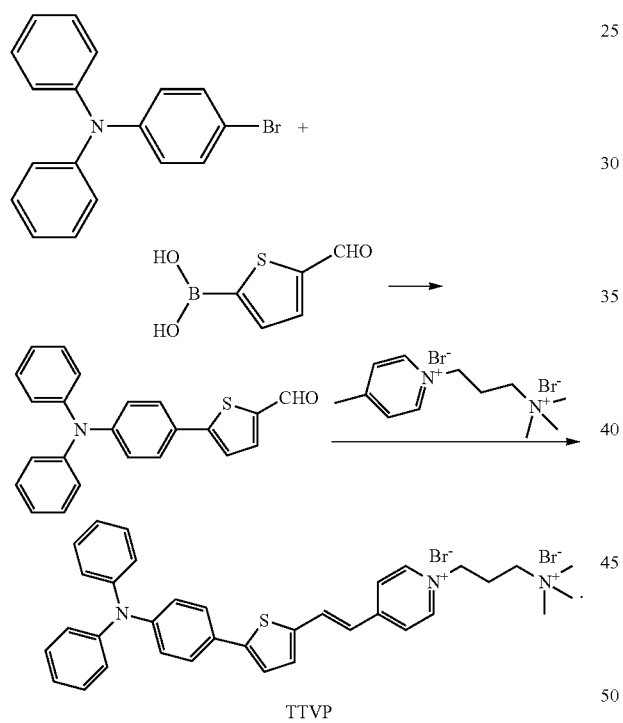

TTVP

Cell Imaging

The present compounds can be effectively utilized as plasma-membrane specific bio-probes in cell imaging. As described in detail herein, the plasma membrane of cells stained with one or more of the present compounds can be clearly visualized with excellent image contrast to the cell background whether or not the cells are washed after cell staining. In addition, optimal fluorescent imaging quality can even be achieved when the cells are stained for a very short period of time, e.g., approximately 30 seconds. In an embodiment, the cells are stained with one or more of the present compounds for a time period ranging from about 30 seconds to about 6 hours. For example, the cells can be stained for a period of time ranging from about 30 seconds to about 10 minutes. It is believed that the plasma-membrane specificity of the present compounds can be attributed to the hydrophilic nature of the compounds. For example, the hydrophilicity of the compounds can impede permeation of the compounds through hydrophobic regions of the phospholipid bilayer of the plasma membrane. The present compounds exhibit high sensitivity to polarity and can be used for indication of environmental polarity. It is believed that the emitting moiety of the present compounds can be embedded in the hydrophobic region of the plasma membrane with low polarity.

One or more of the fluorescent compounds can be contacted with a cell and an imaging method can then be used to visualize a cellular target of interest. The target of interest can be, for example, a plasma membrane of the cell. Contacting the target cell with one or more of the present compounds can include embedding one or more of the present compounds in a hydrophobic region of the plasma membrane. The hydrophobic region can have low polarity. The imaging method can include, for example, fluorescence microscopy or confocal laser scanning microscopy.

Cancer Therapy

The present compounds can efficiently generate reactive oxygen species (ROS) in vivo when irradiated with visible light. As such, the compounds can be effective in killing cancer cells through image-guided, photodynamic therapy (PDT) processes. PDT is a promising approach to cancer treatment because of the precise controllability, minimal invasive nature, and high spatiotemporal accuracy it offers.

A method of killing cancer cells can include contacting a target cancer cell with one or more of the present compounds, imaging the target cancer cell while the one or more compounds contacts the target cancer cell, and subjecting the target cancer cell to white light irradiation while the one or more compounds contacts the target cancer cell. The imaging method can be selected from fluorescence microscopy and confocal laser scanning microscopy.

As described herein, the fluorescent compounds can efficiently generate ROS under white light irradiation to kill the cancer cells. In dark conditions, however, the fluorescent compounds demonstrate low cytotoxicity. As such, the fluorescent compounds can be successfully used as photosensitizers in photodynamic therapy (PDT) applications.

The present teachings are illustrated by the following examples.

EXAMPLES

Materials and Instruments

Dulbecco's Modified Essential Medium (DMEM) and RPMI-1640 were purchased from Gibco (Life Technologies). Phosphate buffered saline (PBS), fetal bovine serum (FBS), penicillin, streptomycin, and DiO were purchased from Thermo Fisher Scientific. H2DCF-DA was purchased from Sigma-Aldrich. Pd(dppf)Cl$_2$, piperidine, 4-bromo-N, N-diphenylaniline, (5-formylthiophen-2-yl)boronic acid, 3-bromo-N,N,N-trimethylpropan-1-aminium bromide and 4-methylpyridine were purchased from Sigma-Aldrich, J&K or MERYER. All the chemicals were used as received without further purification. 1-(3-Trimethylammoniopropyl)-4-methylpyridinium dibromide and 5-(4-(diphenylamino)phenyl)thiophene-2-carbaldehyde were synthesized according to the literature method.

H spectra were measured on Bruker ARX 400 NMR spectrometers using CD$_3$OD as the deuterated solvent. High-resolution mass spectra (HRMS) were recorded on a Finnegan MAT TSQ 7000 Mass Spectrometer System operating in a MALDI-TOF mode. UV absorption spectra were taken on a Milton Ray Spectronic 3000 array spectrophotometer. Steady-state fluorescence spectra were recorded on a Perkin Elmer LS 55 spectrometer. Fluorescence images were collected on Olympus BX 41 fluorescence microscope. Laser confocal scanning microscope images were collected on Zeiss laser scanning confocal microscope (LSM7 DUO) and analyzed using ZEN 2009 software (Carl Zeiss).

For cell culturing, HeLa cells were cultured in the MEM containing 10% FBS and antibiotics (100 units/mL penicillin and 100 mg/mL streptomycin) in a 5% $CO_2$ humidity incubator at 37° C.

For cell imaging, cells were grown in a 35 mm Petri dish with a coverslip at 37° C. The live cells were incubated with a certain dye at a certain concentration for a certain time. After adding TTVP (500 nM), the Petri dish was shaken for a few seconds at room temperature, then the coverslip was removed. The TTVP-labelled cells were mounted and imaged using a laser scanning confocal microscope (LSM7 DUO) at 512 nm with 5% laser power (the scanning rate was 22.4 s per frame). The emission filter was 600-744 nm.

For confocal colocalization, after incubating HeLa cells with DiO at 37° C. for 10 min, TTVP was added into the culture, which was then shaken for a few seconds at room temperature. The medium was then removed and the cells were rinsed with PBS three times and then imaged under confocal microscope.

For photostability studies, TTVP-labelled HeLa cells were imaged by a confocal microscope (Zeiss laser scanning confocal microscope LSM7 DUO) using ZEN 2009 software (Carl Zeiss). Conditions: for TTVP, excitation wavelength: 488 nm; for DiO, excitation wavelength: 488 nm (5% laser power).

For cytotoxicity studies relating to biocompatibility of the present compounds to Hela cells, MTT assays were used to evaluate the cytotoxicity of the presented AIEgens. Cells were seeded in 96-well plates (Costar, IL, USA) at a density of 6000-8000 cells/well. After overnight culturing, medium in each well were replaced by 100 µL fresh medium containing different concentrations of TTVP. 24 hours later, 10 µL MTT solution (5 mg/mL in PBS) was added into each well. After 4 hours of incubation, 100 µL SDS-HCl aqueous solution (10% SDS and 0.01 M HCl) was added to each well. After incubation for 4 hours, the absorption of each well at 595 nm was recorded via a plate reader (Perkin-Elmer Victor3™). Each trial was performed with 6 wells parallel.

For cytotoxicity studies relating to cytotoxicity of the present compounds to cancer cells under light irradiation, HeLa cells were seeded in 96-well plates (Costar, IL, USA) at a density of 6000-8000 cells/well. After overnight culturing, medium in each well were replaced by 100 µL fresh medium containing different concentrations of TTVP. After incubation for 3 s, plates containing HeLa cells were exposed to white light (around 10 mW) for 10 min, and another array of plates with cells were kept in dark as control. Then the plates were subjected to the same treatment as the biocompatibility test.

Quantitative data were expressed as mean±standard deviation. Statistical comparisons were made by ANOVA analysis and Student's t-test. P value <0.05 was considered statistically significant.

Example 1

Synthesis of TTVP

A solution of 5-(4-(diphenylamino)phenyl)thiophene-2-carbaldehyde (71 mg, 0.2 mmol) and 1-(3-Trimethylammoniopropyl)-4-methylpyridinium dibromide (71 mg, 0.2 mmol) was refluxed under nitrogen in dry ethanol catalyzed by a few drops of piperidine overnight. After cooling to room temperature, the solvent was removed by evaporation under reduced pressure. The residue was purified by a neutral aluminum oxide column using DCM and methanol mixture (98:2 v/v) as eluting solvent to give a red brown powder of TTVP (98 mg, 71% of yield). $^1H$ NMR (400 MHz, $CD_3OD$), δ (ppm): 8.78 (d, J=6.8 Hz, 2H), 8.13-8.17 (m, 3H), 7.58-7.60 (m, 2H), 7.48 (d, J=4.0 Hz, 1H), 7.40 (d, J=4.0 Hz, 1H), 7.30-7.34 (m, 4H), 7.02-7.12 (m, 9H), 4.60 (t, J=7.8 Hz, 2H), 3.52-3.56 (m, 2H), 3.20 (s, 9H), 2.51-2.59 (m, 2H). $^{13}C$ NMR (100 MHz, $CDCl_3$), δ (ppm): 155.99, 150.81, 150.19, 148.72, 145.26, 140.33, 136.72, 135.83, 130.81, 128.12, 126.40, 125.16, 125.04, 124.90, 123.80, 121.71, 64.04, 58.04, 54.13, 26.27. ESI HRMS: calcd. for $C_{35}H_{37}Br_2N_3S$ $[M-Br]^+$: 610.1886, found: 610.1874.

Example 2

Photophysical Properties

Figure 2:
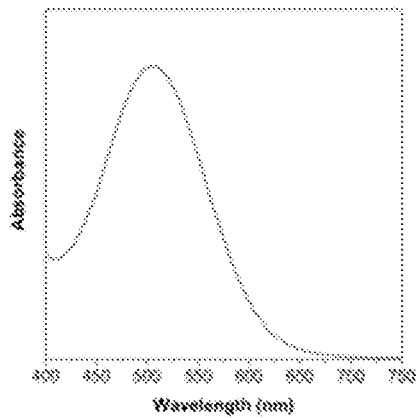
FIG. 2 depicts UV-vis absorption spectrum of the aqueous solution of TTVP.
Figure 3A:
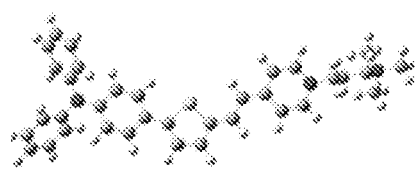
FIG. 3A depicts optimized molecular geometry of TTVP by the DFT calculations.
Figure 3B:
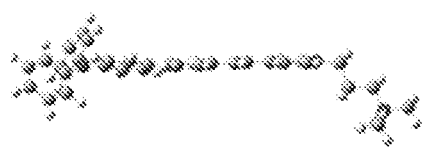
FIG. 3B depicts a side-view of the optimized molecular geometry.
Figure 3C:
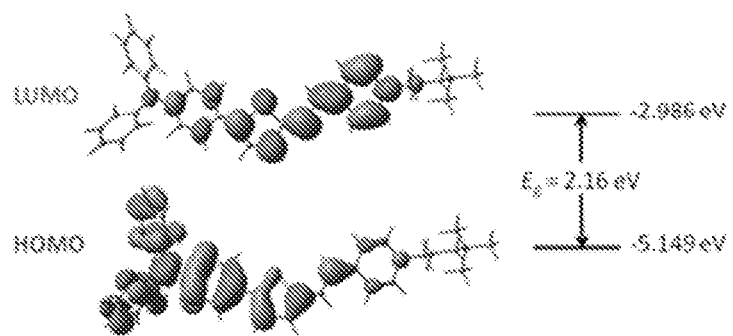
FIG. 3C depicts molecular orbital amplitude plots of HOMO and LUMO energy levels of TTVP (Eg (energy gap)=LUMO−HOMO).

TTVP has good water solubility. TTVP benefits from its positively charged amine and pyridinium salt having hydrophilic characteristic, as well as the small size of the hydrophobic moiety. The aqueous solution of TTVP displayed a maximum absorption band peaked at 515 nm with 33517 $M^{-1}$ $cm^{-1}$ of molar extinction coefficient (FIG. 2). The relatively long absorption wavelength can be attributed to its small HOMO-LOMO energy gap, which is caused by the strong electron donating-accepting interaction of the emitting center (FIGS. 3A-3C).

Figure 1C:
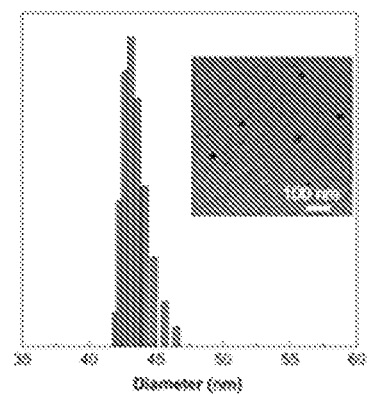
FIG. 1C depicts particle size distributions of TTVP aggregates in water/THF mixture with 90% THF fraction (Concentration: 10 μM. Inset: TEM spectrum of TTVP aggregates in water/THF mixture with 90% THF fraction).

The investigation of AIE features in water/THF mixtures with different THF fractions ($f_T$) demonstrated that TTVP is a typical AIE-active molecule (FIG. 1A). It is almost non-emissive in aqueous solution in a single molecule state, and the photoluminescence (PL) intensity gradually increased when the fraction of THF increased due to the formation of nanoaggregates (FIG. 1C). The strongest PL intensity was observed at 90% fraction of THF upon aggregation, in which the PL intensity was enhanced to about 97.3 times that of aqueous solution (FIG. 1B). As shown in Table 1, its maximum emission in the aggregated state was located at 708 nm, indicating both its NIR-emissive property and large Stokes shift.

TABLE 1

Optical properties of AIEgen TTVP.

| $\lambda_{abs}$ (nm)[a] | ε ($M^{-1}$ $cm^{-1}$) | $\lambda_{em}$ (nm) | | Solid ($\Phi_F$)[b,c] | $\alpha_{AIE}$ ($I_{aggr, max}$/ $I_{soln}$) | $\tau^d$ (ns) |
|---|---|---|---|---|---|---|
| | | Soln | Aggr | | | |
| 515 | 33517 | N/A | 708 | 705 (2.7%) | 97.3 | 0.92 |

[a]Absorption maximum in aqueous solutions.
[b]Emission maximum in solid state.
[c]Fluorescence quantum yield determined by a calibrated integrating sphere.
[d]Fluorescence lifetime, measured under ambient conditions.

Figure 4:
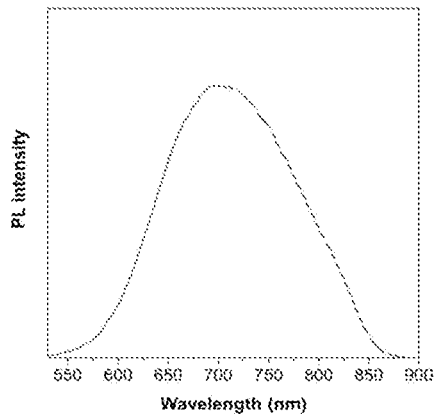
FIG. 4 depicts PL spectrum of TTVP in the solid state.
Figure 5:
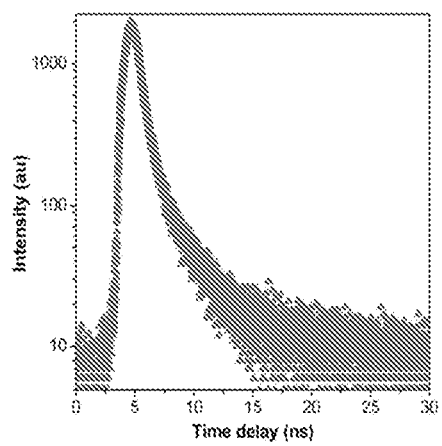
FIG. 5 depicts the fluorescence decay curve of TTVP in the solid state.

Dynamic light scattering analysis (DLS) and transmission electron microscope (TEM) measurements were performed to confirm the formation of aggregates upon the addition of THF into the TTVP aqueous solution. DLS revealed that the average hydrodynamic diameter of these nanoaggregates that formed in the suspension containing 90% fraction of THF was around 43 nm with a polydispersity index of 0.13, while their spherical morphology was observed by TEM analysis. In the solid state, TTVP emitted at 705 nm with 2.7% of quantum yield and 0.92 ns of lifetime (FIGS. 4-5, Table 1).

Figure 7A:
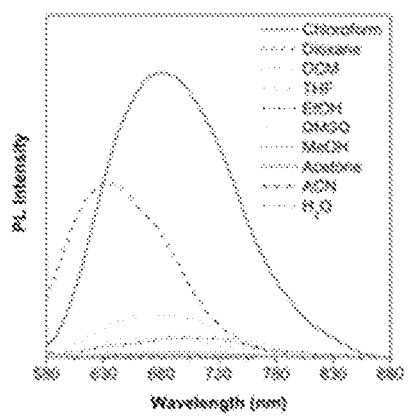
FIG. 7A depicts PL spectra of TTVP in solvents with different polarities (Concentration: 0.5 μM; excitation wavelength: 515 nm).
Figures 10A, 10B, 10C, 10D:
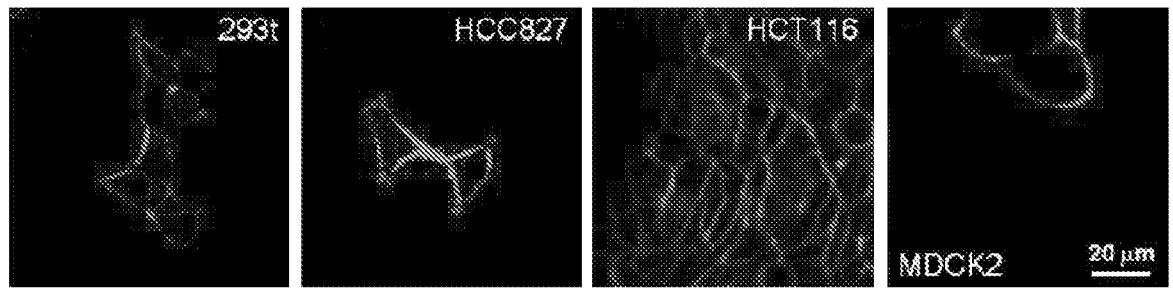
FIGS. 10A, 10B, 10C, and 10D depict confocal images of living 293T cells, HCC827 cells, HCT116 cells, and MDCK2 cells, respectively, after incubation with TTVP (500 nM) for an extremely short incubation period (around 3 s) (λex: 488 nm (1% laser power, 0.05 μW)).

Solvatochromism studies showed that, with the increase of solvent polarity, the emission maximum of TTVP largely red-shifted while emission intensity was considerably reduced (FIGS. 7A-7B), suggesting a strong twisted intramolecular charge transfer (TICT) effect.

Example 3

Cell Imaging

Figure 6A:
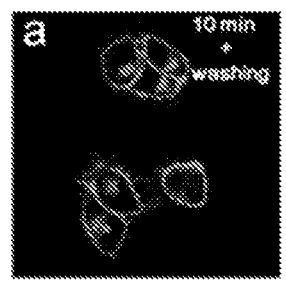
FIG. 6A depicts a confocal image of living HeLa cells after incubation with TTVP (500 nM) for 10 minutes using a washing procedure after incubation.
Figure 6B:
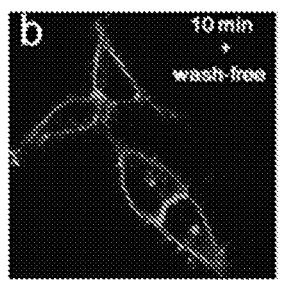
FIG. 6B depicts a confocal image of living HeLa cells after incubation with TTVP (500 nM) for 10 minutes using a wash-free procedure after incubation.
Figure 6C:
FIG. 6C depicts a confocal image of living HeLa cells after incubation with TTVP (500 nM) for 5 minutes using a wash-free procedure after incubation.
Figure 6D:
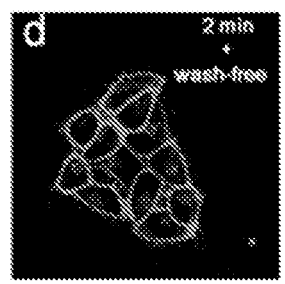
FIG. 6D depicts a confocal image of living HeLa cells after incubation with TTVP (500 nM) for 2 minutes using a wash-free procedure after incubation.
Figure 6E:
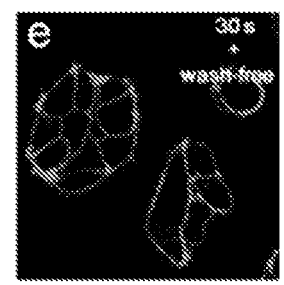
FIG. 6E depicts a confocal image of living HeLa cells after incubation with TTVP (500 nM) for 30 seconds using a wash-free procedure after incubation.
Figure 6F:
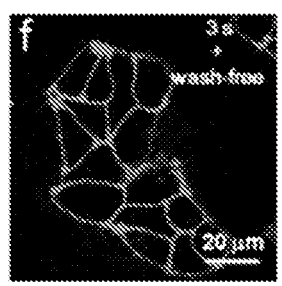
FIG. 6F depicts a confocal image of living HeLa cells after incubation with TTVP (500 nM) for a short incubation period (around 3 s) using a wash-free procedure after incubation ($\lambda_{ex}$: 488 nm (1% laser power, 0.05 μW).
Figure 6G:
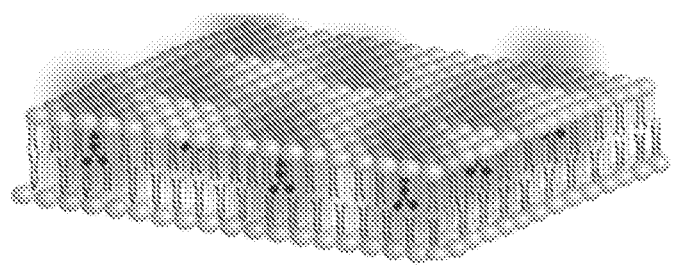
FIG. 6G depicts a schematic illustration of plasma membrane-specific imaging with TTVP (Scale bar=20 μm).
Figure 6H:
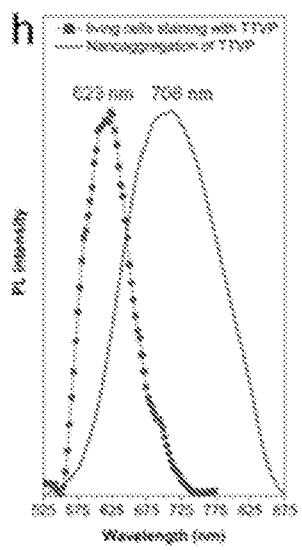
FIG. 6H depicts fluorescence spectrum of plasma membrane of living HeLa cells stained with TTVP, and fluorescence spectrum of TTVP nano-aggregation.

As a water-soluble NIR-emissive AIEgen, TTVP maintains an "off" state in an aqueous environment. As such, TTVP can serve as a "light-up" probe for bioimaging with minimal background interference from both free dyes and bio-substrate autofluorescence. In preliminary bioimaging experiments, cell imaging studies were conducted using HeLa cells as a cell model, and incubating 500 nM of TTVP for 10 min. It was observed that the plasma membrane of the cells can be clearly visualized with excellent image contrast to the cell background whether or not the cells were washed after cell staining (FIGS. 6A-6B). The influence of incubation period was then investigated by utilizing a wash-free procedure with different staining times. The results demonstrated that no obvious change of fluorescent imaging quality in terms of both fluorescence intensity and specificity was found with the reduction of staining time from 10 min to 30 s (FIGS. 6A-6E). Surprisingly, the plasma membrane lit up significantly when the staining process included simply shaking the culture with cells at room temperature for a few seconds after adding TTVP (FIG. 6F), indicating the ultrafast staining (staining in a matter of seconds) characteristic. On the other hand, when the staining time was increased to 4 h, the plasma membrane could still be clearly visualized. A majority of TTVP entered the cells after staining for 6 hours, resulting in strong emission from within the cell (FIGS. 8A-8D). The plasma membrane-staining ability of TTVP can be mainly attributed to its good hydrophilicity, which impedes the permeation of TTVP passing through the hydrophobic region of phospholipid bilayers. It is believed that the emitting moiety of TTVP is embedded within the hydrophobic region with low polarity, evidently giving fluorescent emission upon irradiation according to the restriction of intramolecular motions (RIM) mechanism of the AIE process (FIG. 6G). Indeed, the maximum emission of living HeLa cells stained with TTVP was located at 623 nm (FIG. 6H); the blue-shifted emission from 708 to 623 nm was likely caused by the low polarity of the surrounding environment of TTVP in living cells, strongly validating the hypothesis that TTVP is embedded in the hydrophobic region of the plasma membrane. Additionally, ultrafast staining could result from the excellent monodispersity of TTVP in culture media of cells.

The specificity of TTVP to plasma membrane was evaluated by co-staining with DiO, which is a commercially available bioprobe for plasma membrane. In this co-localization experiment, after incubating HeLa cells with DiO for 10 min, TTVP was added into the culture followed by culture shaking for a few seconds at room temperature. In order to accommodate the staining protocol of DiO, post-washing after cell staining was carried out. As shown in FIGS. 9A-9H, TTVP can selectively accumulate in the plasma membrane and emit strong red fluorescence. The well-merged images of TTVP and DiO indicate the high specificity of the compounds to the plasma membrane, and the Pearson's correlation coefficient is determined to be 89%. To assess the photostability of TTVP and DiO, continuous excitation and sequential scanning with confocal microscope were utilized. The results show that the emission intensity of TTVP slightly decreased within 15 min irradiation (FIGS. 9E and 9F), and the fluorescence loss of DiO was very obvious upon irradiation under the same conditions (FIGS. 9G and 9H), demonstrating the superior photostability of TTVP to that of DiO.

Encouraged by the distinct advantages of TTVP for membrane-specific imaging, this ultrafast staining and wash-free cellular imaging protocol was further employed for staining other cell lines, including 293T, HCC827, HCT116, and MDCK2. In all tested cases, the plasma membrane was clearly visualized with high S/N ratio of cell imaging with intense red emission (FIGS. 10A-10D), suggesting the high tolerance of TTVP to cell types.

Example 4

ROS Generation

Figure 11A:
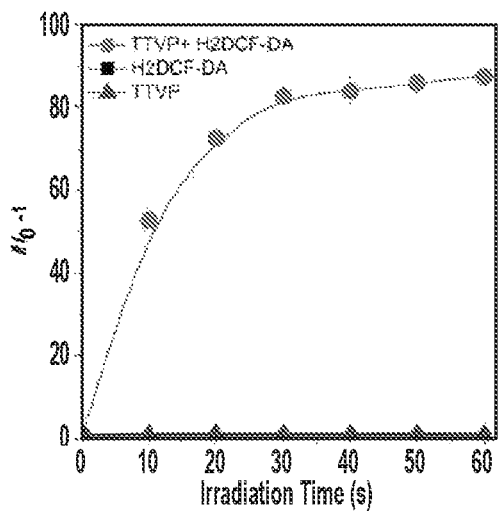
FIG. 11A is a graph depicting relative change in fluorescent intensity ($I/I_0-1$) at 534 nm of H2DCF-DA, TTVP, and mixtures of H2DCF-DA and TTVP in PBS upon white light irradiation for different times. Concentrations: 10 μM (TTVP) and 5 μM (H2DCF-DA) (Light Power: 10 mW).
Figure 11B:
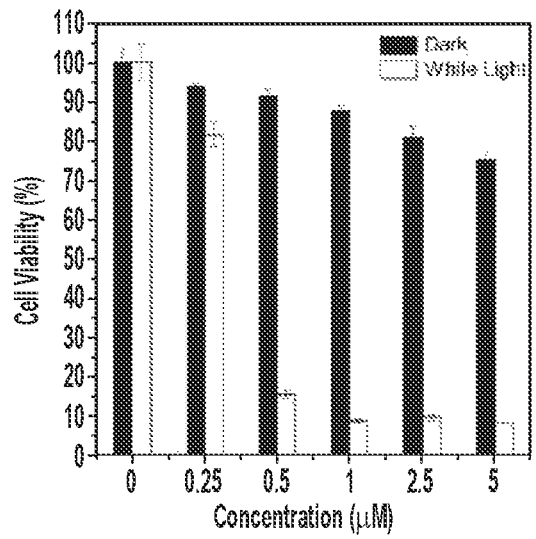
FIG. 11B is a graph depicting cell viability of HeLa cells stained with different concentrations of TTVP in the absence of white light irradiation or the presence of white light irradiation for 10 min (light power: 10 MW).

The strong absorption of TTVP in the visible light region permits utilization of visible light as the excitation light source for PDT processes. Visible light causes less damage to biological systems than UV light. The ROS generation efficiency of TTVP was initially determined by the use of H2DCF-DA as an indicator, which emits fluorescence with a "turn on" process triggered by ROS. As depicted in FIG. 11A, TTVP or H2DCF-DA alone was non-emissive or weekly emissive, and each fluorescence intensity remained almost constant within 60 s white light irradiation. On the contrary, in the presence of TTVP, the emission intensity of H2DCF-DA was gradually enhanced with increasing exposure time to white light, reaching 87-fold within 60 s (FIGS. 11B-11I). The efficient ROS generation of TTVP could be attributed to both its small singlet-triplet energy gap (0.47 eV) and excellent monodispersity. The former favors the improvement of the yield of the triplet excited state, and the latter can enlarge contact area between TTVP and oxygen.

Example 5

Photodynamic Therapy

Figure 11C:
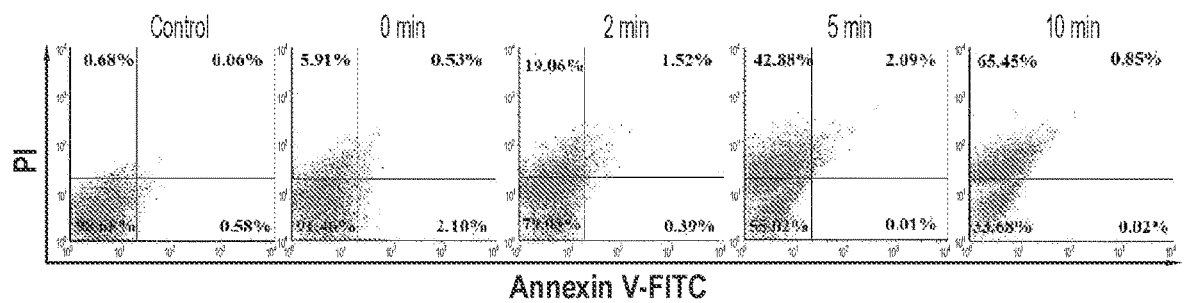
FIG. 11C depicts cell apoptosis and necrosis analysis using flow cytometer with Annexin V-FITC/PI double staining after different treatments (Concentrations: 500 nM (TTVP)).
Figure 11D:
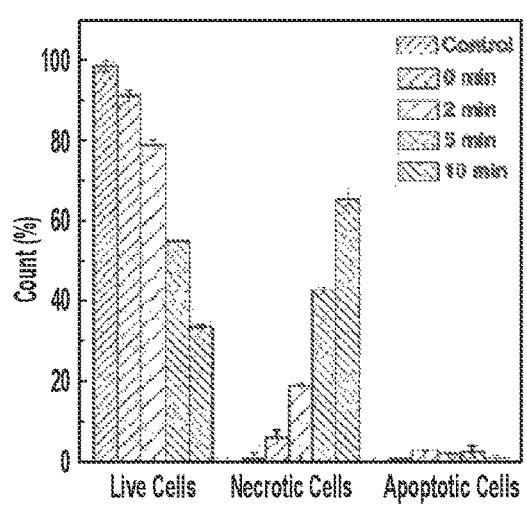
FIG. 11D is a graph providing statistical analysis of the flow cytometry data provided in FIG. 11C.
Figures 11E, 11F, 11G, 11H, 11I:
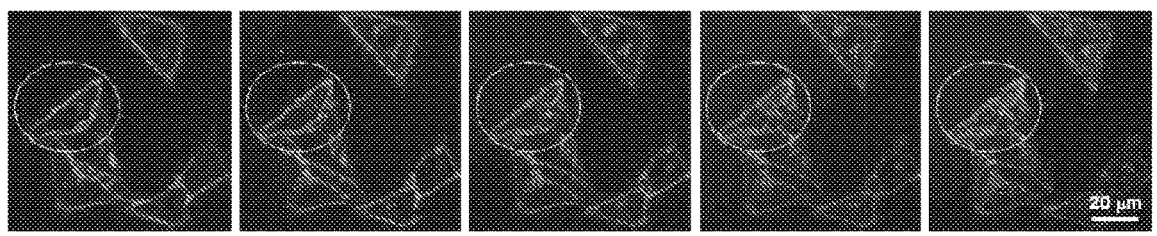
FIGS. 11E, 11F, 11G, 11H, and 11I depict confocal images of living HeLa cells stained with TTVP through continuous laser irradiation. $\lambda_{ex}$: 488 nm (20% laser power, 0.925 μW).
Figures 12A, 12B, 12C, 12D, 12E:
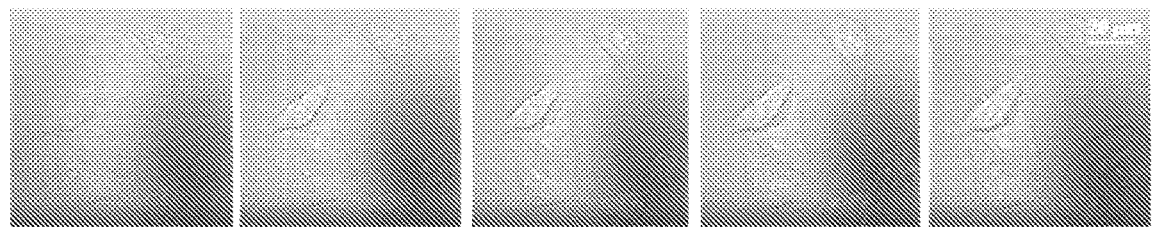
FIGS. 12A, 12B, 12C, 12D, and 12E depict bright-field confocal images of HeLa cells stained with TTVP upon the increase of irradiation time. $\lambda_{ex}$: 488 nm (20% laser power, 0.925 μW).

Effective ROS generation of the present compounds in PDT applications was quantitatively evaluated on HeLa cells by a standard MTT assay. A dose-dependent toxicity was determined in both the absence and presence of white light irradiation. The results demonstrate that TTVP exhibits low cytotoxicity in dark conditions, which is one of the essential features of photosensitizers for PDT application. The HeLa cell viability dropped rapidly to 15% with concentration of 500 nM, and 1 µM of TTVP caused almost complete cell death with white light irradiation (FIG. 11B), indicating its remarkable efficiency for cancer cell ablation by the PDT pathway. In comparison, HeLa cells retained 90% viability when they were incubated with 1 µM of TTVP in dark conditions. Furthermore, flow cytometric analysis using Annexin V-FITC/propidium iodide (PI) double staining was utilized to determine cell apoptosis (FIGS. 11C and 11D). It was observed that light irradiation caused cancer cell necrosis in a short period of time, and the ratio of necrotic cells significantly increased with prolonging the irradiation time, which suggested the high efficiency of TTVP in photodynamic ablation of cancer cells. It is worth noting that continuous light irradiation with strong power (around 18.5 times higher than that for cell imaging depicted in FIGS. 6A-6H and FIGS. 8A-8H) led to some changes of cells, for instance, TTVP can gradually enter the cells (FIGS. 11E-11I); the cell membrane morphology changed, and the formation of blebs on the plasma membrane was clearly observed, which is a sign of cell death. Those changes can be attributed to the fact that the ROS generated from TTVP considerably disrupts the rigidity and permeability of plasma membrane, and induces cancer cell death. FIGS. 12A, 12B, 12C, 12D, and 12E depict bright-field confocal images of HeLa cell stained with TTVP upon the increase of irradiation time. $\lambda_{ex}$: 488 nm (20% laser power, 0.925 µW).

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A fluorescent compound exhibiting aggregation induced emission properties and near infrared absorption, the compound having a backbone structural formula selected from the group consisting of:

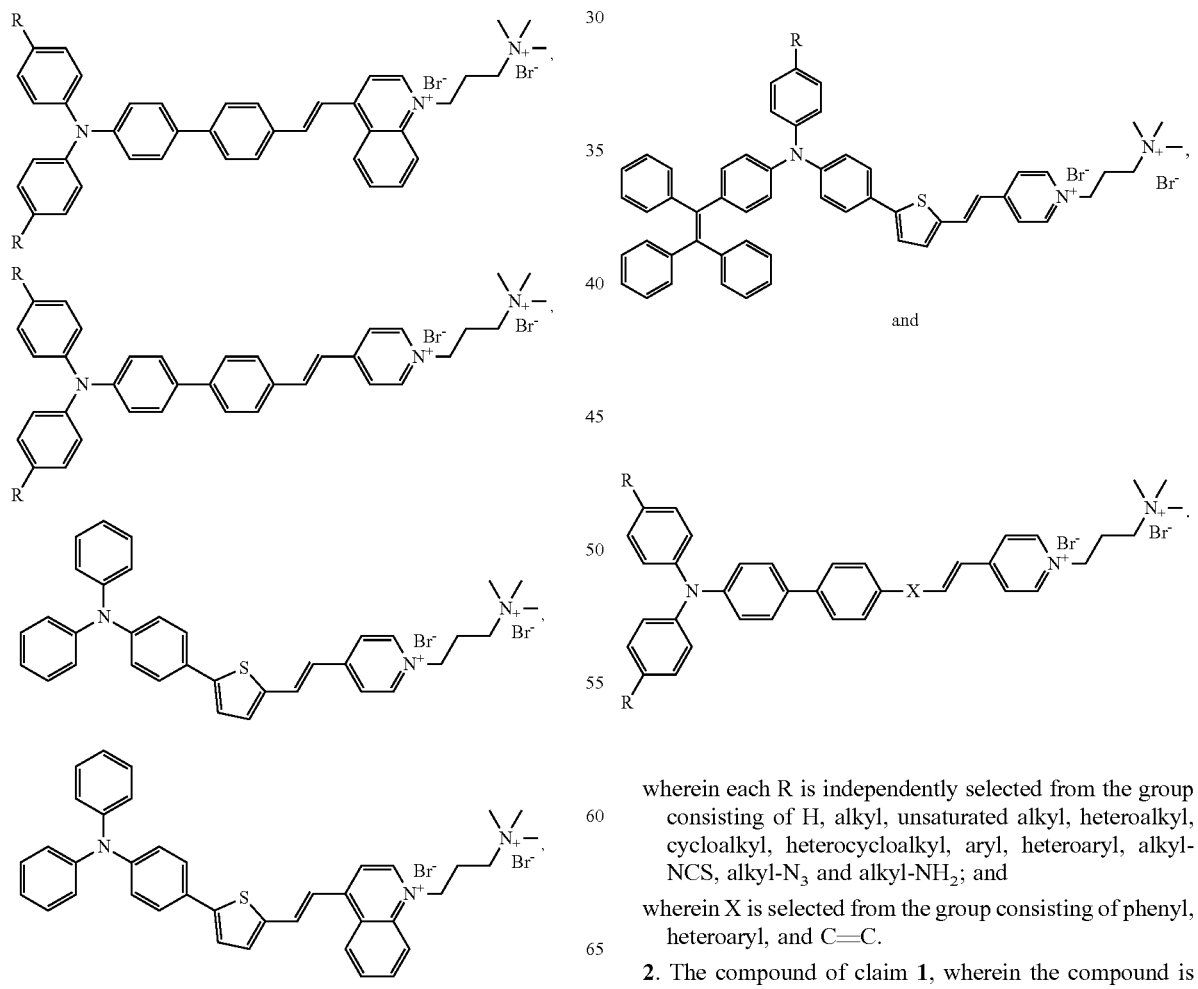

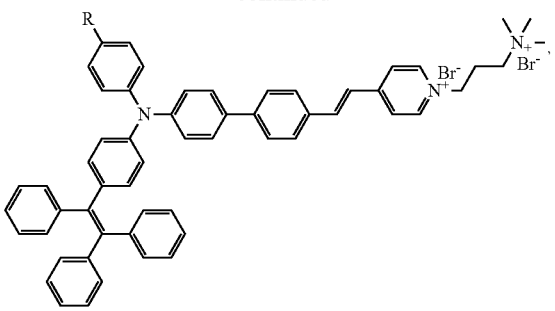

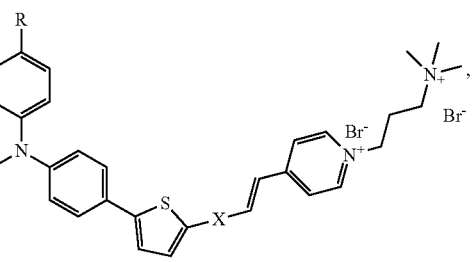

and wherein each R is independently selected from the group consisting of H, alkyl, unsaturated alkyl, heteroalkyl, cycloalkyl, heterocycloalkyl, aryl, heteroaryl, alkyl-NCS, alkyl-$N_3$ and alkyl-$NH_2$; and wherein X is selected from the group consisting of phenyl, heteroaryl, and C=C.

2. The compound of claim 1, wherein the compound is water-soluble.

3. The compound according to claim 1, wherein the compound is:

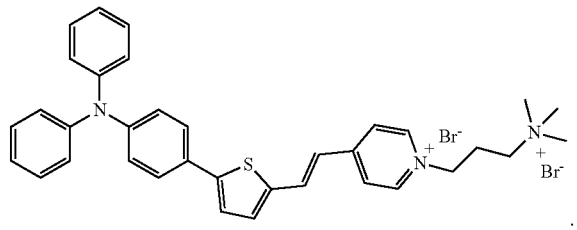

4. A method of cellular imaging, comprising:
contacting a target cell with the compound of claim 1; and
identifying a cellular target of interest using an imaging method.

5. The method of claim 4, wherein the cellular target of interest comprises a plasma membrane of the target cell.

6. The method of claim 5, wherein contacting the target cell with the compound comprises embedding the compound in a hydrophobic region of the plasma membrane.

7. The method of claim 6, wherein the compound is embedded in the hydrophobic region with low polarity.

8. The method of claim 4, wherein the imaging method is selected from the group consisting of fluorescence microscopy and confocal laser scanning microscopy.

9. A method of generating reactive oxygen species, comprising irradiating the compound of claim 1 with white light.

10. A method of killing cancer cells, comprising:
contacting a target cancer cell with the compound of claim 1;
imaging the target cancer cell while the compound contacts the target cancer cell using an imaging method; and
subjecting the target cancer cell to white light irradiation while the compound is contacting the target cancer cell to kill the target cancer cell.

11. The method of claim 10, wherein the imaging method is selected from the group consisting of fluorescence microscopy and confocal laser scanning microscopy.

12. A fluorescent compound exhibiting aggregation induced emission properties and near infrared absorption, wherein the compound is:

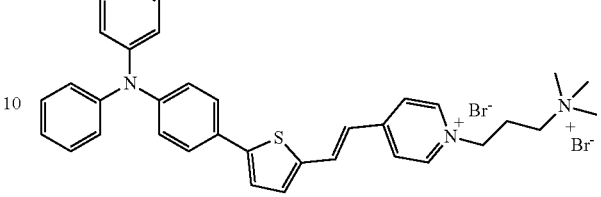

13. A method of cellular imaging, comprising:
contacting a target cell with the compound of claim 12; and
identifying a cellular target of interest using an imaging method.

14. The method of claim 13, wherein the cellular target of interest comprises a plasma membrane of the target cell.

15. The method of claim 14, wherein contacting the target cell with the compound comprises embedding the compound in a hydrophobic region of the plasma membrane.

16. The method of claim 15, wherein the compound is embedded in the hydrophobic region with low polarity.

17. The method of claim 13, wherein the imaging method is selected from the group consisting of fluorescence microscopy and confocal laser scanning microscopy.

18. A method of generating reactive oxygen species, comprising irradiating the compound of claim 12 with white light.

19. A method of killing cancer cells, comprising:
contacting a target cancer cell with the compound of claim 12;
imaging the target cancer cell while the compound contacts the target cancer cell using an imaging method; and
subjecting the target cancer cell to white light irradiation while the compound is contacting the target cancer cell to kill the target cancer cell.

20. The method of claim 19, wherein the imaging method is selected from the group consisting of fluorescence microscopy and confocal laser scanning microscopy.

* * * * *